United States Patent [19]
Andersen et al.

[11] Patent Number: 5,827,856
[45] Date of Patent: Oct. 27, 1998

[54] METHOD OF TREATING INSULIN RESISTANCE

[75] Inventors: Knud Erik Andersen, Smørum; Rolf Hohlweg, Kvistgaard; Tine Krogh Jørgensen, Herlev; Peter Madsen, Bagsværd; Henrik Sune Andersen, København; Uffe Bang Olsen, Vallensbæk, all of Denmark; Polivka Zdenek, Praha, Switzerland; Silhánková Alexandra, Praha, Switzerland; Sidelár Karel, Praha, Switzerland

[73] Assignee: Novo Nordisk A/S, Bagsvaerd, Denmark

[21] Appl. No.: 627,750

[22] Filed: Apr. 2, 1996

[30] Foreign Application Priority Data

Apr. 7, 1995 [DK] Denmark .................. 0413/95
Sep. 11, 1995 [DK] Denmark .................. 1001/95

[51] Int. Cl.$^6$ .................................................. A01N 43/42
[52] U.S. Cl. .................. 514/297; 514/290; 514/298; 514/432; 514/437; 514/454

[58] Field of Search ...................... 514/290, 297, 514/298, 432, 437, 454

[56] References Cited

FOREIGN PATENT DOCUMENTS 0 221 572   5/1987   European Pat. Off. .
221572      5/1987   European Pat. Off. .

OTHER PUBLICATIONS

Dorland's Illustrated Medical Dictionary, Edition 28, 1994.
Pavia et al., J. Med. Chem., vol. 35, pp. 4238–4248, (1992).
Falch et al., Drug Design & Delivery, vol. 4, pp. 205–215, (1989).

*Primary Examiner*—Marianne M. Cintins
*Assistant Examiner*—Dwayne C. Jones
*Attorney, Agent, or Firm*—Steve T. Zelson; Elias J. Lambiris

[57] ABSTRACT

The present invention provides a novel method for the clinical treatment of painful, hyperalgesic and/or inflammatory conditions in which C-fibers play a pathophysiological role by eliciting neurogenic pain or inflammation.

16 Claims, No Drawings

METHOD OF TREATING INSULIN RESISTANCE

FIELD OF THE INVENTION

The present invention provides a novel method for the clinical treatment of painful, hyperalgesic and/or inflammatory conditions in which C-fibers play a pathophysiological role by eliciting neurogenic pain or inflammation. The invention also relates to the use of the present compounds for the treatment of insulin resistance in non-insulin-dependent diabetes mellitus (NIDDM) or aging, the present compounds knowing to interfere with neuropeptide containing C-fibres and hence inhibit the secretion and circulation of insulin antagonizing peptides like CGRP or amylin.

BACKGROUND OF THE INVENTION

The nervous system exerts a profound effect on the inflammatory response. Antidromic stimulation of sensory nerves results in localized vasodilation and increased vascular permeability (Janecso et al. Br. J. Pharmacol. 1967, 31, 138–151) and a similar response is observed following injection of peptides known to be present in sensory nerves. From this and other data it is postulated that peptides released from sensory nerve endings mediate many inflammatory responses in tissues like skin, joint, urinary tract, eye, meninges, gastrointestinal and respiratory tracts. Hence inhibition of sensory nerve peptide release and/or activity, may be useful in treatment of, for example arthritis, dermatitis, rhinitis, asthma, cystitis, gingivitis, thrombophlelitis, glaucoma, gastro-intestinal diseases or migraine.

Further, the potent effects of CGRP on skeletal muscle glycogen synthase activity and muscle glucose metabolism, together with the notion that this peptide is released from the neuromuscular junction by nerve excitation, suggest that CGRP may play a physiological role in skeletal muscle glucose metabolism by directing the phosphorylated glucose away from glycogen storage and into the glycolytic and oxidative pathways (Rossetti et al. Am. J. Physiol. 264, E1–E10, 1993). This peptide may represent an important physiological modulator of intracellular glucose trafficing in physiological conditions, such as exercise, and may also contribute to the decreased insulin action and skeletal muscle glycogen synthase in pathophysiological conditions like NIDDM or aging-associated obesity (Melnyk et al. Obesity Res. 3, 337–344, 1995) where circulating plasma levels of CGRP are markedly increased. Hence inhibition of release and/or activity of the neuropeptide CGRP may be useful in the treatment of insulin resistance related to type 2 diabetes or aging.

In U.S. Pat. No. 4,383,999 and No. 4,514,414 and in EP 236342 as well as in EP 231996 some derivatives of N-(4,4-disubstituted-3-butenyl)-azaheterocyclic carboxylic acids are claimed as inhibitors of GABA uptake. In EP 342635 and EP 374801, N-substituted azaheterocyclic carboxylic acids in which an oxime ether group and vinyl ether group forms part of the N-substituent respectively are claimed as inhibitors of GABA uptake. Further, in WO 9107389 and WO 9220658, N-substituted azacyclic carboxylic acids are claimed as GABA uptake inhibitors. EP 221572 claims that 1-aryloxyalkyl-pyridine-3-carboxylic acids are inhibitors of GABA uptake.

DESCRIPTION OF THE INVENTION

The method of this invention comprises administering to a patient suffering from neurogenic inflammation an effective amount of a compound of formula I

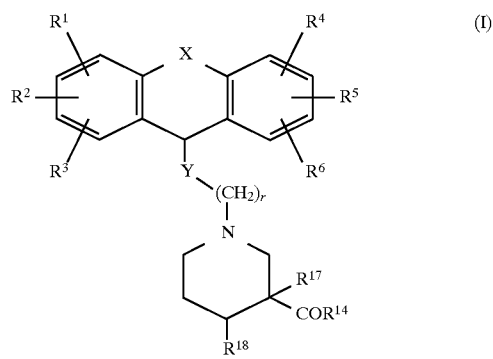

wherein $R^1$, $R^2$, $R^3$, $R^4$, $R^5$ and $R^6$ independently are hydrogen, halogen, trifluoromethyl, hydroxy, $C_{1-6}$-alkyl, $C_{1-6}$-alkoxy, $-NR^7R^8$ or $-SO_2NR^7R^8$ wherein $R^7$ and $R^8$ independently are hydrogen or $C_{1-6}$-alkyl; and X is completion of an optional bond, $-CH_2-$, $-CH_2CH_2-$, $-CH=CH-$, $-O-$, $-S(O)_z-$ wherein z is 0, 1 or 2, or $NR^9$ wherein $R^9$ is hydrogen or $C_{1-6}$-alkyl; and Y is $-O-$, $-S(O)_q-$ wherein q is 0, 1 or 2, or $NR^{10}$ wherein $R^{10}$ is hydrogen or $C_{1-6}$-alkyl; and r is 1, 2, 3 or 4; and $R^{14}$ is hydroxy, $C_{1-6}$-alkoxy or $NR^{15}R^{16}$ wherein $R^{15}$ and $R^{16}$ independently are hydrogen or $C_{1-6}$-alkyl; and $R^{17}$ is hydrogen; and $R^{18}$ is hydrogen or hydroxy or may together with $R^{17}$ represent a bond;

or a pharmaceutically acceptable salt thereof.

The compounds of formula I may exist as geometric and optical isomers and all isomers and mixtures thereof are included herein. Isomers may be separated by means of standard methods such as chromatographic techniques or fractional crystallization of suitable salts.

The compounds according to the invention may optionally exist as pharmaceutically acceptable acid addition salts or—when the carboxylic acid group is not esterified—as pharmaceutically acceptable metal salts or—optionally alkylated—ammonium salts.

Examples of such salts include inorganic and organic acid addition salts such as hydrochloride, hydrobromide, sulphate, phosphate, acetate, fumarate, maleate, citrate, lactate, tartrate, oxalate or similar pharmaceutically acceptable inorganic or organic acid addition salts, and include the pharmaceutically acceptable salts listed in Journal of Pharmaceutical Science, 66, 2 (1977) which are hereby incorporated by reference.

The term "$CC_{1-6}$-alkyl" as used herein, alone or in combination, refers to a straight or branched, saturated hydrocarbon chain having 1 to 6 carbon atoms such as e.g. methyl, ethyl, n-propyl, isopropyl, n-butyl, sec-butyl, isobutyl, tert-butyl, n-pentyl, 2-methylbutyl, 3-methylbutyl, n-hexyl, 4-methylpentyl, neopentyl, n-hexyl, 1,2-dimethylpropyl, 2,2-dimethylpropyl and 1,2,2-trimethylpropyl.

The term "$C_{1-6}$-alkoxy" as used herein, alone or in combination, refers to a straight or branched monovalent substituent comprising a $C_{1-6}$-alkyl group linked through an ether oxygen having its free valence bond from the ether oxygen and having 1 to 6 carbon atoms e.g. methoxy, ethoxy, propoxy, isopropoxy, butoxy, pentoxy.

The term "halogen" means fluorine, chlorine, bromine or iodine.

Illustrative examples of compounds encompassed by the present invention include:

1-(2-(10,11-Dihydro-5H-dibenzo[a,d]cyclohepten-5-yloxy)ethyl)-3-piperidinecarboxylic acid;

1-(2-(10,11-Dihydro-5H-dibenzo[a,d]cyclohepten-5-yloxy)ethyl)-4-hydroxy-3-piperidinecarboxylic acid;

1-(2-(10,11-Dihydro-5H-dibenzo[a,d]cyclohepten-5-yloxy)ethyl)-1,2,5,6-tetrahydro-3-pyridinecarboxylic acid;

1-(2-(9,10-Dihydroanthracen-9-yloxy)ethyl)-3-piperidinecarboxylic acid;

1-(2-(9H-Xanthen-9-yloxy)ethyl)-3-piperidinecarboxylic acid;

1-(2-(9H-Thioxanthen-9-yloxy)ethyl)-3-piperidinecarboxylic acid;

or a pharmaceutically acceptable salt thereof.

As used herein, the term "patient" includes any mammal which could benefit from treatment of neurogenic pain or inflammation or insulin resistance in NIDDM. The term particularly refers to a human patient, but is not intended to be so limited.

It has been demonstrated that the novel compounds of formula I inhibit neurogenic inflammation which involves the release of neuropeptides from peripheral and central endings of sensory C-fibres. Experimentally this can be demonstrated in animal models of formalin induced pain or paw oedema (Wheeler and Cowan, Agents Actions 1991, 34, 264–269) in which the novel compounds of formula I exhibit a potent inhibitory effect. Compounds of formula I may be used to treat all painful, hyperalgesic and/or inflammatory conditions in which C-fibers play a pathophysiological role by eliciting neurogenic pain or inflammation, i.e.:

Acutely painful conditions exemplified by migraine, postoperative pain, burns, bruises, post-herpetic pain (Zoster) and pain as it is generally associated with acute inflammation; chronic, painful and/or inflammatory conditions exemplified by various types of neuropathy (diabetic, posttraumatic, toxic), neuralgia, rheumatoid arthritis, spondylitis, gout, inflammatory bowel disease, prostatitis, cancer pain, chronic headache, coughing, asthma, chronic pancreatitis, inflammatory skin disease including psoriasis and autoimmune dermatoses, osteoporotic pain.

Further, it has been demonstrated that the compounds of general formula I improves the glucose tolerance in diabetic ob/ob mice and that this may result from the reduced release of CGRP from peripheral nervous endings. Hence the compounds of general formula I may be used in the treatment of NIDDM as well as aging-associated obesity. Experimentally this has been demonstrated by the subcutaneous administration of glucose into ob/ob mice with or without previous oral treatment with a compound of general formula I.

The compounds of formula I may be prepared by the following method:

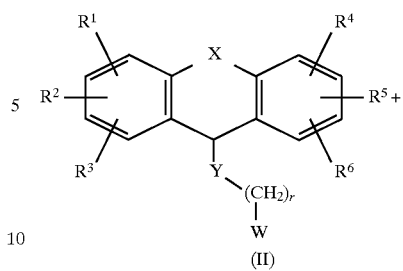

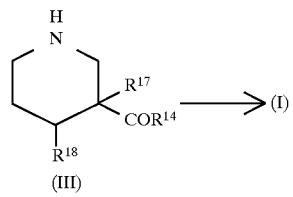

A compound of formula II wherein $R^1$, $R^2$, $R^3$, $R^4$, $R^5$, $R^6$, X, Y and r are as defined above and W is a suitable leaving group such as halogen, p-toluene sulphonate or mesylate may be reacted with an azaheterocyclic compound of formula III wherein $R^{14}$, $R^{17}$ and $R^{18}$ are as defined above. This alkylation reaction may be carried out in a solvent such as acetone, dibutylether, 2-butanone, methyl ethyl ketone, ethyl acetate, tetrahydrofuran (THF) or toluene in the presence of a base e.g. potassium carbonate and a catalyst, e.g. an alkali metal iodide at a temperature up to reflux temperature for the solvent used for e.g. 1 to 120 h. If esters have been prepared in which $R^{14}$ is alkoxy, compounds of formula I wherein $R^{14}$ is OH may be prepared by hydrolysis of the ester group, preferably at room temperature in a mixture of an aqueous alkali metal hydroxide solution and an alcohol such as methanol or ethanol, for example, for about 0.5 to 6 h.

Compounds of formula II and III may readily be prepared by methods familiar to those skilled in the art.

Under certain circumstances it may be necessary to protect the intermediates used in the above methods e.g. a compound of formula III with suitable protecting groups. The carboxylic acid group can, for example, be esterified. Introduction and removal of such groups is described in "Protective Groups in Organic Chemistry" J. F. W. McOrnie ed. (New York, 1973).

PHARMACOLOGICAL METHODS

Formalin induced pain or paw oedema

Values for in vivo inhibition of formalin induced pain or oedema for the compounds of the present invention were assessed in mice essentially by the method of Wheeler-Aceto and Cowan (Agents Action 1991, 34, 265–269).

About 20 g NMRI female mice were injected 20 μl 1% formalin into the left hind paw. The animals were then placed on a heated (31° C.) table, and the pain response was scored. After 1 hour they were killed and bled. Left and right hind paws were removed and the weight difference between the paws indicates the oedema response of the formalin injected paw.

Reduced release of CGRP ob/ob female mice, 16 weeks of age, where injected glucose (2g/kg) subcutaneously. At times hereafter blood glucose was determined in tail venous blood by the glucose oxidase method. At the end of the study the animals were decapitated and trunck blood collected. Immunoreactive CGRP was determined in plasma by radio-immuno-assay. Two groups of animals were used. The one group was vehicle treated, whereas the other group received a compound of formula I via drinking water (100 mg/l) for five days before the test.

For the above indications the dosage will vary depending on the compound of formula I employed, on the mode of administration and on the therapy desired. However, in general, satisfactory results are obtained with a dosage of from about 0.5 mg to about 1000 mg, preferably from about 1 mg to about 500 mg of compounds of formula I conveniently given from 1 to 5 times daily, optionally in sustained release form. Usually, dosage forms suitable for oral administration comprise from about 0.5 mg to about 1000 mg, preferably from about 1 mg to about 500 mg of the compounds of formula I admixed with a pharmaceutical carrier or diluent.

The compounds of formula I may be administered in pharmaceutically acceptable acid addition salt form or where possible as a metal or a lower alkyl-ammonium salt. Such salt forms exhibit approximately the same order of activity as the free base forms.

This invention also relates to pharmaceutical compositions comprising a compound of formula I or a pharmaceutically acceptable salt thereof and, usually, such compositions also contain a pharmaceutical carrier or diluent. The compositions containing the compounds of this invention may be prepared by conventional techniques and appear in conventional forms, for example capsules, tablets, solutions or suspensions.

The pharmaceutical carrier employed may be a conventional solid or liquid carrier. Examples of solid carriers are lactose, terra alba, sucrose, talc, gelatin, agar, pectin, acacia, magnesium stearate and stearic acid. Examples of liquid carriers are syrup, peanut oil, olive oil and water.

Similarly, the carrier or diluent may include any time delay material known to the art, such as glyceryl monostearate or glyceryl distearate, alone or mixed with a wax.

If a solid carrier for oral administration is used, the preparation can be tabletted, placed in a hard gelatin capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatin capsule or sterile injectable liquid such as an aqueous or non-aqueous liquid suspension or solution.

Generally, the compounds of this invention are dispensed in unit dosage form comprising 50–200 mg of active ingredient in or together with a pharmaceutically acceptable carrier per unit dosage.

The dosage of the compounds according to this invention is 1–500 mg/day, e.g. about 100 mg per dose, when administered to patients, e.g. humans, as a drug.

A typical tablet which may be prepared by conventional tabletting techniques contains

| Core: | |
|---|---|
| Active compound (as free compound or salt thereof) | 100 mg |
| Colloidal silicon dioxide (Areosil ®) | 1.5 mg |
| Cellulose, microcryst. (Avicel ®) | 70 mg |

| -continued | |
|---|---|
| Modified cellulose gum (Ac-Di-Sol ®) | 7.5 mg |
| Magnesium stearate | |
| Coating: | |
| HPMC approx. | 9 mg |
| *Mywacett ® 9–40 T approx. | 0.9 mg |

*Acylated monoglyceride used as plasticizer for film coating.

The route of administration may be any route which effectively transports the active compound to the appropriate or desired site of action, such as oral or parenteral e.g. rectal, transdermal, subcutaneous, intranasal, intramuscular, topical, intravenous, intraurethral, ophthalmic solution or an ointment, the oral route being preferred.

EXAMPLES

The process for preparing compounds of formula I is further illustrated in the following examples, which, however, are not to be construed as limiting.

Hereinafter, TLC is thin layer chromatography and THF is tetrahydrofuran, $CDCl_3$ is deuterio chloroform and DMSO-$d_6$ is hexadeuterio dimethylsulfoxide. The structures of the compounds are confirmed by either elemental analysis or NMR, where peaks assigned to characteristic protons in the title compounds are presented where appropriate. NMR shifts (δ) are given in parts per million (ppm). M.p. is melting point and is given in °C. Column chromatography was carried out using the technique described by W. C. Still et al, J. Org. Chem. 1978, 43, 2923–2925 on Merck silica gel 60 (Art. 9385). Compounds used as starting materials are either known compounds or compounds which can readily be prepared by methods known per se.

EXAMPLE 1

1-(2-(10,11-Dihydro-5H-dibenzo[a,d]cyclohepten-5-ylsulfanyl)ethyl)-3-piperidinecarboxylic acid hydrochloride 5-Chloro-10,11-dihydro-5H-dibenzo[a,d]cycloheptene (6.86 g, 0.030 mol) and thiourea (2.28 g, 0.030 mol) were dissolved in ethanol (50 ml) and heated at reflux temperature for 2.5 h. After cooling to room temperature, 2 N sodium hydroxide (20 ml) was added and the mixture was subsequently heated to reflux temperature under a nitrogen atmosphere for 2 h. The reaction mixture was cooled to room temperature, made acidic by addition of a slight excess of sulfuric acid and extracted with diethyl ether (50 ml). The organic phase was washed with water (50 ml) and brine (30 ml). Evaporation in vacuo afforded 6.78 g (100%) of 10,11-dihydro-5H-dibenzo[a,d]cyclohepten-5-thiol as an oil. The crude product was directly used in the next step without further purification.

A solution of the above crude thiol (4.53 g, 0.020 mol) in absolute ethanol (7 ml) was added dropwise to a stirred solution of sodium ethoxide, freshly prepared from absolute ethanol (25 ml) and sodium (0.46 g, 0.020 mol). Stirring was continued for 0.5 h at ambient temperature. 1-Bromo-2-chloroethane (8.60 g, 0.060 mol) was added dropwise and the reaction mixture was stirred at ambient temperature for 16 h. The mixture was diluted with toluene (20 ml) and filtered. The filtrate was evaporated in vacuo and stripped with toluene, affording 5.72 g (99%) of crude 5-(2-chloroethylsulfanyl)-10,11-dihydro-5H-dibenzo[a,d]cycloheptene as an oil.

The above crude chloride (5.72 g, 0.020 mol) was dissolved in 2-pentanone (20 ml). Ethyl 3-piperidinecarboxylate (3.11 g, 0.020 mol), potassium carbonate (8.0 g) and potassium iodide (3.0 g) were added and the mixture was heated at reflux temperature for 7 h. The reaction mixture was cooled to room temperature, diluted with diethyl ether (40 ml) and filtered. The filtrate was evaporated in vacuo, and the remainder was redissolved in dichloromethane (50 ml) and washed with 2 N hydrochloric acid. The organic phase was washed with saturated aqueous sodium bicarbonate until no further evolution of carbon dioxide occurred, washed with water and evaporated in vacuo. The remaining oil was redissolved in diethyl ether (60 ml). The crude product was precipitated as its hydrochloride salt by addition of excess of of hydrogen chloride in diethyl ether. The sticky hydrochloride was dissolved in dichloromethane (50 ml) and washed with 2 N sodium hydroxide (50 ml), water (50 ml) and brine (50 ml). The organic phase was dried ($MgSO_4$) and the solvent was evaporated, affording 2.80 g (35%) of 1-(2-(10,11-dihydro-5H-dibenzo[a,d]cyclohepten-5-ylsulfanyl)ethyl)-3-piperidine carboxylic acid ethyl ester as an oil.

TLC: $R_f$=0.55 ($SiO_2$:heptane/ethylacetate=1:1).

The above ester (1.23 g, 0.003 mol) was dissolved in ethanol (15 ml). 2 N Sodium hydroxide (4.0 ml) was added and the mixture was stirred for 1 h at room temperature. The solution was made acidic (pH 1) by addition of excess 1 N hydrochloric acid and concentrated in vacuo to remove ethanol. The remainder was extracted with diethyl ether (50 ml) and redissolved in dichloromethane (50 ml). The organic phase was dried ($Na_2SO_4$) and concentrated in vacuo. Crystallisation of the remainder from acetone (20 ml) afforded 0.78 g (62%) of the title compound as a crystalline powder.

M.p. 201–205° C.

Calculated for $C_{23}H_{27}NO_2S$, HCl:

C, 66.09%; H. 6.75%; N, 3.35%; Found:

C, 66.08%; H, 6.93%; N, 3.29%. cl EXAMPLE 2

1-(2-(10,11-Dihydro-5H-dibenzo[a,d]cyclohepten-5-ylsulfinyl)ethyl)-3-piperidinecarboxylic acid hydrochloride 1-(2-(10,11-Dihydro-5H-dibenzo[a,d]cyclohepten-5-ylsulfanyl)-ethyl)-3-piperidinecarbo-xylic acid ethyl ester (0.82 g, 0.002 mol, prepared as described in example 1), was dissolved in ethanol (5 ml). Under initial cooling in an icebath, solid sodium periodate (0.51 g, 0.0024 mol) was added, and the reaction mixture was stirred at room temperature for 16 h. The solvent was then evaporated in vacuo and the remainder redissolved in dichloromethane (20 ml). The mixture was washed with water (50 ml) and brine (30 ml) and subsequently dried ($Na_2SO_4$). After evaporation in vacuo, the crude product was purified by column chromatography on silica gel (80 g) using a mixture of ethyl acetate and pyridine (97.5:2.5) as eluent. This afforded 0.14 g (16%) of 1-(2-(10,11-dihydro-5H-dibenzo[a,d]cyclohepten-5-ylsulfinyl)ethyl)-3-piperidinecarboxylic acid ethyl ester as a syrup.

The above ester (0.14 g, 0.33 mmol) was dissolved in ethanol (5 ml). 2 N Sodium hydroxide (0.5 ml) was added and the mixture was stirred for 1.5 h at room temperature. The solution was made acidic (pH 1) by addition of 1 N hydrochloric acid and concentrated in vacuo to remove ethanol. The remainder was extracted with diethyl ether (20 ml) and redissolved in dichloromethane (20 ml). The organic phase was dried ($Na_2SO_4$) and concentrated in vacuo. Crystallisation of the remainder from acetone (3 ml) afforded 0.027 g (20%) of the title compound as a crystalline powder.

M.p. 140–145° C.

MS(FAB) 398.1 $(M+1)^+$

EXAMPLE 3

(R)-1-(2-(3-Chloro-10,11-dihydro-5H-dibenzo[a,d]cyclohepten-5-yloxy)-1-ethyl)-3-piperidinecarboxylic acid hydrogenoxalate To a solution of 3-chloro-10,11-dihydro-5H-dibenzo[a,d]cyclohepten-5-ol (3.52 g, 0.014 mol, prepared similarly as described in Fr.M. 2165, 1963; Chem.Abstr. 60, 14523 (1963)) and 2bromoethanol (2.5 g, 0.02 mol) in benzene (80 ml), concentrated sulfuric acid (0.85 ml) was added dropwise. The reaction mixture was stirred for 1.5 h, diluted with 50 ml of benzene and washed with water (30 ml), 0.6 N $NaHCO_3$ (20 ml) and 2×30 ml of water. The benzene solution was dried ($MgSO_4$) and the solvent was evaporated under vacuum to give a residue which was crystallised from a mixture of cyclohexane and n-hexane. 3.9 g (77%) of 5-(2-bromoethoxy)-3-chloro-10,11-dihydro-5H-dibenzo[a,d]cycloheptene was obtained.

The above bromide (4.2 9, 0.012 mol) was dissolved in N,N-dimethylformamide (120 ml). To this solution (R)-3-piperidinecarboxylic acid ethyl ester tartrate (7.37 g, 0.024 mol) and potassium carbonate (16.5 g, 0.12 mol) were added and the mixture was heated at 55° C. for 7 h. After cooling to the room temperature, the reaction mixture was diluted with 250 ml of benzene and 100 ml of water. After stirring for 15 minutes the layers were separated, washed (3×100 ml water), dried ($K_2CO_3$) and the solvent was evaporated under vacuum. The residue was further purified by column chromatography on silica gel (120 g) using chloroform as eluent. This afforded 5.05 g (99%) of (R)-1-(2-(3-chloro-10,11-dihydro-5H-dibenzo[a,d]cyclohepten-5-yloxy)-1-ethyl)-3-piperidinecarboxylic acid ethyl ester as an oil.

TLC: $R_f$=0.40 ($SiO_2$; chloroform).

The above ester (5.18 g, 0.01 mol) was dissolved in ethanol (50 ml) and 15% of sodium hydroxide (30 ml) was added. The mixture was stirred at 50° C. for 2.5 h, cooled, diluted with water (50 ml) and acetic acid was added (4.0 g) to pH=5.5. The resulting mixture was extracted with chloroform (100 ml, 2×50 ml), the combined organic extracts were washed with water (50 ml), dried ($Na_2SO_4$) and evaporated under vacuum. The residue was dissolved in acetone (25 ml) at 55° C., oxalic acid was added (6.57 g, 0 015 mol) and then the hot solution was precipitated with 25 ml dry diethyl ether. The mixture was stirred for 1 h, filtered and the solid was washed with diethyl ether (3×20 ml). This afforded 4.02 g (82%) of the title compound.

M.p. 90–94° C.

$[\alpha]^{20}_d$=−6.65 ° (0.4%, EtOH).

Calculated for $C_{23}H_{28}ClNO_3$:, $C_2H_2O_4$:

C, 61.28%; H, 5.76%; N, 2.86%; Found:

C, 61.22%; H, 6.01%; N, 2.85%.

We claim:

1. A method of treating insulin resistance in a subject in need thereof comprising administering to the subject an effective amount of a compound of formula I

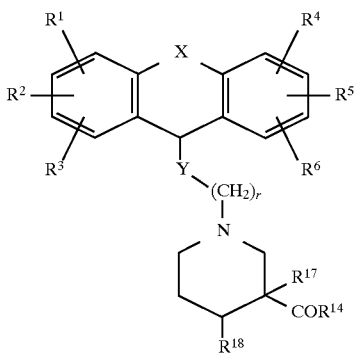

wherein

R¹, R², R³, R⁴, R⁵ and R⁶ independently are hydrogen, halogen, trifluoromethyl, hydroxy, $C_{1-6}$-alkyl, $C_{1-6}$-alkoxy, -NR⁷R⁸ or -SO₂NR⁷R⁸ wherein R⁷ and R⁸ independently are hydrogen or $C_{1-6}$-alkyl;

X is completion of an optional bond, —CH₂—, —CH₂CH₂—, —CH=CH—, —O—, —S(O)$_z$— wherein z is 0, 1 or 2, or NR⁹ wherein R⁹ is hydrogen or $C_{1-6}$-alkyl;

Y is —O—, —S(O)$_q$— wherein q is 0, 1 or 2, or NR¹⁰ wherein R¹⁰ is hydrogen or $C_{1-6}$-alkyl;

r is 1, 2, 3 or 4;

R¹⁴ is hydroxy, $C_{1-6}$-alkoxy or NR¹⁵R¹⁶ wherein R¹⁵ and R¹⁶ independently are hydrogen or $C_{1-6}$-alkyl;

R¹⁷ is hydrogen; and

R¹⁸ is hydrogen or hydroxy or may together with R¹⁷ represent a bond; or a pharmaceutically acceptable salt thereof.

2. A method according to claim 1 wherein R¹, R², R³, R⁴, R⁵ and R⁶ independently are hydrogen, halogen, trifluoromethyl or $C_{1-6}$-alkoxy.

3. A method according to claim 1 wherein X is —CH₂CH₂—, —CH=CH— or —S(O)$_z$— wherein z is 0 or 1.

4. A method according to claim 3 wherein X is —CH₂CH₂—.

5. A method according to claim 1 wherein Y is —O—, —S— or S(O)q when q is 0 or 1.

6. A method according to claim 1 wherein r is 2 or 3.

7. A method according to claim 1 wherein R¹⁴ is hydroxy.

8. The method according to claim 1 wherein the compound is:

1-(2-(10,11-Dihydro-5H-dibenzo[a,d]cyclohepten-5-yloxy)ethyl)-3-piperidinecarboxylic acid or a pharmaceutically acceptable salt thereof.

9. The method according to claim 1 wherein the compound is:

1-(2-(10,11-Dihydro-5H-dibenzo[a,d]cyclohepten-5-yloxy)ethyl)-4-hydroxy-3-piperidinecarboxylic acid or a pharmaceutically acceptable salt thereof.

10. The method according to claim 1 wherein the compound is:

1-(2-(10,11-Dihydro-5H-dibenzo[a,d]cyclohepten-5-yloxy)ethyl)-1,2,5,6-tetrahydro-3-pyridinecarboxylic acid or a pharmaceutically acceptable salt thereof.

11. The method according to claim 1 wherein the compound is:

1-(2-(9,10-Dihydroanthracen-9-yloxy)ethyl)-3-piperidinecarboxylic acid or a pharmaceutically acceptable salt thereof.

12. The method according to claim 1 wherein the compound is:

1-(2-(9H-Xanthen-9-yloxy)ethyl)-3-piperidinecarboxylic acid or a pharmaceutically acceptable salt thereof.

13. The method according to claim 1 wherein the compound is:

1-(2-(9H-Thioxanthen-9-yloxy)ethyl)-3-piperidinecarboxylic acid or a pharmaceutically acceptable salt thereof.

14. The method according to claim 1 wherein the compound is:

1-(2-(10,11-Dihydro-5H-dibenzo[a,d]cyclohepten-5-ylsulfanyl)ethyl)-3-piperidinecarboxylic acid or a pharmaceutically acceptable salt thereof.

15. The method according to claim 1 wherein the compound is:

1-(2-(10,11-Dihydro-5H-dibenzo[a,d]cyclohepten-5-ylsulfinyl)ethyl)-3-piperidinecarboxylic acid or a pharmaceutically acceptable salt thereof.

16. The method according to claim 1 wherein the compound is:

(R)-1-(2-(3-Chloro-10,11-dihydro-5H-dibenzo[a,d]cyclohepten-5-yloxy)-1-ethyl)-3-piperidinecarboxylic acid hydrogenoxalate or a pharmaceutically acceptable salt thereof.

* * * * *

UNITED STATES PATENT AND TRADEMARK OFFICE
CERTIFICATE OF CORRECTION

PATENT NO. : 5,827,856

DATED : October 27, 1998

INVENTOR(S) : Andersen et al.

It is certified that error appears in the above-identified patent and that said Letters Patent is hereby corrected as shown below:

Col. 10, line 28, new claim 13, delete "piperidinecarboxylicacidoraphamaceutically" and insert --piperidinecarboxylic acid or a pharmaceutically--

Signed and Sealed this

Twenty-seventh Day of March, 2001

Attest:

NICHOLAS P. GODICI

*Attesting Officer*  *Acting Director of the United States Patent and Trademark Office*